United States Patent
Miller-Jones et al.

(10) Patent No.: US 6,333,157 B1
(45) Date of Patent: Dec. 25, 2001

(54) DISASSOCIATION OF INTERACTING MOLECULES

(75) Inventors: David N. Miller-Jones, Cambridge; Karin Bergmann, West Wratting; Susan L. Watson, Cambridge, all of (GB)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/381,896

(22) PCT Filed: Apr. 2, 1998

(86) PCT No.: PCT/GB98/00975

§ 371 Date: Mar. 31, 2000

§ 102(e) Date: Mar. 31, 2000

(87) PCT Pub. No.: WO98/44100

PCT Pub. Date: Oct. 8, 1998

(30) Foreign Application Priority Data

Apr. 2, 1997 (GB) .................................................. 9706654

(51) Int. Cl.$^7$ .............................. C12Q 1/68; C12P 19/34; C12M 1/34; G01N 33/00; C07H 21/04
(52) U.S. Cl. .......................... 435/6; 435/91.1; 435/287.2; 435/91.2; 436/94; 536/23.1; 536/24.3; 536/24.33
(58) Field of Search ............................. 435/6, 91.1, 91.2, 435/183, 283.1, 287.1, 287.2; 436/94; 536/23.1, 24.3, 24.33, 25.3

(56) References Cited

U.S. PATENT DOCUMENTS

| | | | |
|---|---|---|---|
| 5,213,669 | 5/1993 | Guttman | 204/180.1 |
| 5,935,825 * | 8/1999 | Nishimura et al. | 435/91.2 |
| 6,033,850 * | 3/2000 | Purvis | 435/6 |
| B1 4,683,202 | 11/1990 | Mullis | 435/91 |

FOREIGN PATENT DOCUMENTS

| | | | |
|---|---|---|---|
| 0 541 238 A1 | 5/1993 | (EP) | G01N/27/447 |
| WO 92/04470 * | 3/1992 | (WO) | . |
| WO 93/15224 | 8/1993 | (WO) | C12Q/1/68 |
| WO 95/25177 | 9/1995 | (WO) | C12Q/1/68 |
| WO 97/08293 | 3/1997 | (WO) | C12N/1/06 |
| WO 98/00562 | 1/1998 | (WO) | C12Q/1/68 |
| WO 98/02573 * | 1/1998 | (WO) | . |

OTHER PUBLICATIONS

C.J. Stanley et al., "Amperometric enzyme–amplified immunoassays," *Journal of Immunological Methods*, 112:153–161 (1988).

* cited by examiner

*Primary Examiner*—Ethan Whisenant
*Assistant Examiner*—Frank Lu
(74) *Attorney, Agent, or Firm*—Pillsbury Winthrop LLP

(57) ABSTRACT dsDNA or other interacting molecules, e.g. antibody and antigen, are disassociated by applying an electrical voltage to a solution containing said molecules in a buffer favoring said disassociation e.g. CHES, CAPS OR CAPSO.

28 Claims, 5 Drawing Sheets

Lanes (from left): 1, double-stranded control; 2&3, CHES; 4&5, MOPS; 6&7, CAPS; 8&9, HEPES; 10, heat-denatured control (a)

Lanes (from left): 1, double-stranded control; 2&3, Tris-HCl; 4&5, PIPES; 6&7, TES; 8&9, carbonate; 10, heat-denatured control (b)

⊞ = ds controls

Lane 1, water; 2,5,8,11,14, double stranded controls; 3,6,9,12,and 15, single stranded controls; 4, CAPSO; 7, CAPS; 10, CHES; 13, Tris-HCl; All at 5mm. Tris-HCl and CHES, pH 7.5, CAPS and CAPSO, pH 8.

EA= Electrical Amplification

DISASSOCIATION OF INTERACTING MOLECULES

This application claims benefit of international application PCT/GB98/00975, filed on Apr. 2, 1998.

This invention relates to processes for the treatment of interacting molecules in order to effect a complete or partial disassociation thereof.

Double-stranded DNA (deoxyribonucleic acid) and DNA/RNA (ribonucleic acid) and RNA/RNA complexes in the familiar double helical configuration are produced by the stable interaction of single-stranded molecules. Such complexes in vitro, require aggressive conditions to separate the complementary strands of the nucleic acid. Known methods that are commonly employed for strand separation require the use of high temperatures of at least 60° C. and often 100° C. or use an alkaline pH of 11 or higher or a low pH. Other methods include the use of helicase enzymes such as Rep protein of *E.coli* that can catalyse the unwinding of the DNA in an unknown way, or binding proteins such as 32-protein of *E.coli* phage T4 that act to stabilise the single-stranded form of DNA. The denatured single-stranded DNA produced by the known processes of heat or alkali treatment is used commonly for hybridisation studies or is subjected to amplification cycles.

Such separation is a prerequisite of a number of protocols involving the in vitro manipulation of nucleic acids, one example of which is a reaction that produces multiple copies of target sequences of DNA and which employs a heat-stable polymerase enzyme (U.S. Pat. No. 4,683,202, K. B. Mullis et al). This development, known as the polymerase chain reaction (PCR), is of significant commercial importance and strand separation is normally effected by heating the sample to approximately 95° C. The removal of the need to heat the sample would provide a number of benefits. For example, it allows the design of compact and readily controllable apparatus, and the use of higher fidelity mesophilic enzymes.

WO 92/04470 discloses a process whereby nucleic acid strands are separated by the application of an electric field. The advantages of the electrical method are discussed in greater detail, along with the method's application in amplification reactions such as PCR and ligase chain reaction. Forms of electrochemical cells for carrying out the reaction are described and also the use of "promoter" compounds that enhance the efficiency of denaturation.

Prior to WO92/04470, a number of other workers had described denaturation of DNA in electrochemical cells. However, in none of these cases was single-stranded product left free in solution in useful quantities. Rather, DNA appears to have become irreversibly bound to the surface of the electrode, in which condition it is not available for further participation in processes such as PCR. In the method of electrical denaturation described in WO92/04470, single strands accumulate in solution and their utility and integrity is confirmed by subsequently performing PCR.

In WO92/04470 electrical denaturation of DNA was carried out using an electrode comprising a central rod of glassy carbon encased in a teflon sleeve except at its end. The working electrode was of platinum mesh lying against the teflon sleeve. A calomel reference electrode was used, situated in a side chamber which was connected to the main cell by a capillary tube (see Stanley C. J. et al, J. Immunol. Meth. [1988], 112, 153–161). Using this apparatus the most rapid denaturation was achieved in 15 minutes with the working electrode at a potential of −1V with respect to the reference. The presence of NaCl in the reaction delayed denaturation.

In WO92/04470, a PCR reaction is conducted in which there are repeated denaturation operations conducted using the electrochemical cell described with intervening amplification stages. The denaturation stages are each conducted for a period of five minutes or longer and the total time for the PCR reaction is therefore very extended. Furthermore, the conditions under which the PCR reaction was conducted in WO92/00470 differ from those of the conventional PCR process in that it was not found possible to use a conventional PCR buffer system. In order to obtain denaturation, it was necessary to conduct the process at a much lower ionic strength than would be consistent with such a buffer system. Excluding the promoter methyl viologen, the process was basically conducted in distilled water.

In WO95/25177 we showed it is possible to conduct a denaturation electrochemically considerably faster than is disclosed in WO92/04470 and to conduct an amplification procedure much faster than is disclosed there.

Although the spacing between the two working electrodes in WO92/04470 is not explicitly stated, it was in fact several millimeters.

An improved method is described in WO95/25177 in which a solution containing said nucleic acid is subjected to a voltage applied between electrodes which approach to within 1.5 mm of one another in said solution. This results in a substantial increase in the rate of denaturation such that WO95/25177 contains examples in which complete denaturation of DNA is achieved within 1 to 2 minutes in comparison with denaturation times of at least 25 minutes using the electrode set up of WO92/04470.

It is indicated in WO95/25177 that rather than simply turning the electrical field on and off when conducting PCR using the apparatus described there, one may optionally reverse the field. In WO95/25177, this reversal of the field is seen as being merely an equivalent to turning the field off. In Application GB96139803, periods of zero voltage are used in combination with such field reversals, to further improve the process.

Although the process of Application WO92/04470 can take place in a solution containing only the electrode and the nucleic acid dissolved in water containing a suitable buffer, the process can be facilitated by the presence in the solution containing the nucleic acid of a promoter compound. Methyl viologen or a salt thereof was disclosed as the preferred promoter compound.

It is believed that the positively charged viologen molecules interact between the negatively charged DNA and the negatively charged cathode to reduce electrostatic repulsion therebetween and hence to promote the approach of the DNA to the electrode surface where the electrical field is at its strongest. Accordingly, we expressed a preference in WO92/04470 to employ as promoters compounds having spaced positively charged centres, e.g. bipolar positively charged compounds. Preferably, the spacing between the positively charged centres was to be similar to that in viologens.

WO93/15224 was in turn based on the discovery that multivalent inorganic cations, preferably $Mg^{2+}$, can also act as promoters in such a system with approximately the same efficacy as methyl viologen.

It is thought that large cations such as $Mg^{2+}$ are able to act as a bridge between a negative electrode and negatively charged regions of the double-stranded nucleic acid.

As described in GB9614544.6, it has also been found that lithium ions can also promote denaturation.

The concentration of said promoter cation is preferably from 1 Mm to 50 Mm, more preferably from 5 Mm to 20 Mm, e.g. about 10 Mm.

The rate and extent of denaturation obtainable in such electrochemical systems depends on a number of factors, including the medium in which the nucleic acid is present. Processes used in molecular biology such as nucleic acid hybridisation assays or amplification procedures like PCR are conducted in media containing a buffering agent to maintain optimum Ph for the reactions involved. However, the presence of such a buffering agent is generally adverse to the electrochemical dehybridisation of nucleic acids. This is to some extent overcome by an appropriate choice of promoter, as described above, but it would be highly desirable to develop systems in which the presence of the buffer was substantially less adverse in its impact on the dehybridisation process.

Thus, whilst it is normally found that increasing ionic strength tends to stabilise the interaction between molecules, so that disassociation occurs more readily in the absence of buffers, which are a source of ions contributing to the ionic strength of the medium, we have now found that certain buffers, herein termed "disassociation permissive buffers" allow disassociation to proceed without the addition of disassociation promoting agents such as magnesium or lithium ions, or viologens.

Tris-HCl is an example of a buffer of the type which may be used when suitable promoters are present. As is shown below, the buffers now proposed are superior in their ability to permit disassociation to proceed when compared with Tris-HCl.

Furthermore, the buffers may be used to permit the disassociation of other interacting molecules, especially biomolecules, under the influence of an electrical voltage. The type of interaction between the molecules may in particular be hydrogen bonding.

The mechanism by which the buffers used according to this invention permit or encourage disassociation is not at present fully understood. It may be that disassociation is caused by a local change in pH in the solution in which the electrodes are immersed, such a change occurring in a microlayer adjacent the electrode surface and producing acid conditions at the positive anode and alkaline conditions at the negative cathode. This would be consistent with the fact that DNA can be caused to denature by both acid and alkaline pH. Buffers permitting the temporary and local generation of a relatively low pH, i.e. those which themselves have a $pK_a$ which is relatively high may allow the necessary pH change to occur when other buffers having a lower $pK_a$ would prevent it.

Buffers show maximum buffering capacity when the pH of the solution is the same as the $pK_a$ of the buffer: as the pH moves away from the $pK_a$, buffering capacity is reduced. Therefore, a solution of CHES ($pK_a$ 9.4) at pH 7.5–8.0 has weak buffering capacity, and its pH is readily deflected downwards. We suggest that the hydrogen ions produced at the anode of an electrochemical cell are sufficient to overcome the buffering effect, causing a local lowering of the pH of the medium, which in turn causes denaturation of double-stranded nucleic acids.

When the electric field is turned off, the medium stabilises to its former pH due to the action of the buffering agent.

This ability of the buffer to reversibly "flip" pH in response to an electric field may be related to its $pK_a$ value.

Alternatively, it may be that it is the intercalation of the buffer into the nucleic acid double helix which is responsible for encouraging or permitting denaturation of double-stranded nucleic acids and that by virtue of either the spacing between the charges or the presence of the cyclohexyl ring, the preferred buffers described herein are particularly suited to use in such systems. A combination of these mechanisms may be acting simultaneously.

Accordingly, the present invention provides a process for disassociating interacting molecules, comprising subjecting a liquid containing said molecules to an electrical voltage applied between electrodes under conditions such as to wholly or partially disassociate at least a proportion of said molecules in the presence of an electrical disassociation permissive buffer which is more disassociation permissive than Tris-HCl.

The molecules may be biomolecules and in particular may be nucleic acid molecules associated by hybridisation (so that said disassociation constitutes denaturation of said hybridised nucleic acid molecules) or one of said interacting biomolecules may be an immunological binding partner of the other of said biomolecules. Yet again, one of said interacting biomolecules may be a ligand and the other may be a receptor for said ligand. The molecules may be macromolecules, one or both of which may be charged, as in a DNA duplex for example.

Said buffer preferably has a $pK_a$ of not less than 8.5, more preferably not less than 9.0, most preferably not less than 9.2.

The process is preferably conducted at a pH of from 7 to 9. The buffer chosen will to some extent dictate the pH at which the disassociation reaction can be performed. Where the disassociation is the dehybridisation of nucleic acid strands in contact with a solution containing an enzyme such as a polymerase, the pH may be selected to optimise the activity of the enzyme. Thus the choice of buffer and of enzyme will be related. By way of example, the buffer CHES is particularly preferred for use with "Vent" polymerase, but buffers with higher $pK_a$'s such as CAPS or CAPSO may be a more appropriate choice with enzymes with higher pH optima such as Bst DNA polymerase from *Bacillus stearothermophilus* (pH 8–9), "Deep Vent" (New England Biolabs) from Pyrococcus sp (pH 8.8), Dynazyme II DNA polymerase (Finnzymes Oy) from *Thermus brockianus* (pH 8.5), Taq DNA polymerase and derivatives from *Thermus aquaticus* (pH 8.8), or T4 DNA polymerase from bacteriophage T4 (pH 8.8).

The buffer is preferably CHES, CAPS or CAPSO. The $pK_a$ values of these buffers are quoted in the literature either as working values or as back corrected thermodynamic values, which are a little higher. In relation to the preferred ranges of $pK_a$ quoted above, regard should be had to the thermodynamic values which are: CHES 9.41, CAPS 10.51 and CAPSO 9.71.

The formulae of CHES, CAPS and CAPSO are shown below:

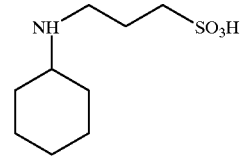
CAPS

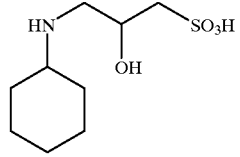
CAPSO

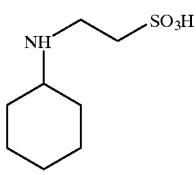
CHES

Preferably the buffer comprises a molecule having a negative charge separated from a positive charge by a distance of from 0.75 to 1.5 times the distance between such charges in CHES, CAPS or CAPSO molecules. Preferably also the buffer has a moiety able to intercalate into double-stranded nucleic acids, e.g. a cyclohexyl substituent.

The process is preferably conducted in from a 5 to 10 mM concentration of said buffer.

It will be understood that the nucleic acid or other molecule does not have to be dissolved in the solution containing the buffer but may be immobilised to a solid phase, immersed in the solution. Thus, preferably, according to the invention, the single-stranded nucleic acid or other released molecule produced is free from the electrode, e.g. dissolved in the solution. However, a nucleic acid may be immobilised on the electrode or another surface in the cell or a coating on the electrode in double or single-stranded form prior to the application of the electric potential, e.g. attached by the end or a small portion intermediate the ends of the nucleic acid chain or through a linker molecule, so as to leave substantial segments of the nucleic acid molecules freely pendant from the electrode surface before and after denaturation. The portion of the nucleic acid by which it is attached is preferably one selected for the purpose by the user.

In addition to said electrode and a counter-electrode, a reference electrode may be contacted with said solution and a voltage may be applied between said electrode and said counter-electrode so as to achieve a desired controlled voltage between said electrode and said reference electrode. The electrodes may be connected by a potentiostat circuit as is known in the electrochemical art.

Preferably, a potential of from −0.5 to −1.5 V is applied to said working electrode with respect to said reference electrode, more preferably from −0.8 to −1.1 V, e.g. about −1.0 V.

Working electrode voltages relative to reference electrodes are given throughout as if measured or as actually measured relative to a calomel reference electrode (BDH No. 309.1030.02).

Thus, optionally, the process may be conducted using a three electrode system of the kind described in WO92/04470 but generally it is preferred that the volume of solution employed according to this invention is small e.g. 1 ml or less, preferably very small e.g. 100 μl or less, e.g. about 25 μl to 40 μl. When using very small reaction volumes of this kind, it will generally not be practical to use a three electrode system. Thus, typically, a voltage will be applied between two electrodes and will be measured directly. Voltages given herein for two electrode systems are given in this way and not with reference to a calomel electrode.

A further alternative preferred form of cell comprises a pair of platinum plate electrodes separated by an elastomer sheet containing a cut out defining the cell cavity. Suitably, the elastomer may have a thickness of from 100 μm to 1 mm, more preferably from 200 μm to 800 μm, most preferably from 300 μm to 500 μm.

It is preferred to apply a voltage difference of from 0.5 to 3 volts between the electrodes. Voltage differences above 3 volts seem to inhibit denaturation or promote degradation although the mechanism involved here is presently unknown.

Preferably, the process is conducted at a voltage of 1.5 to 2.5 volts measured as a voltage difference between the electrodes.

If there is a coating on the electrode, the applied voltage will generally need to be increased to compensate for the voltage drop across the coating.

Optionally, one can conduct the denaturation or disassociation using a constant current supply rather than a regulated voltage and this may serve to compensate for variations in the geometrical set-up of the electrodes between different denaturation or disassociation operations.

Where a constant current regime is employed, it will generally be preferable to use a current of from 80 to 160 μA, e.g. about 100 to 125 μA.

In addition to the lithium promoter of GB9614544.6, one may employ a promoter compound such as methyl viologen as described in WO92/04470 to produce more rapid disassociation or denaturation. Other promoters are described in WO93/15224, i.e. multivalent cations such as magnesium. Other multivalent cations which are effective and which can be used include lanthanum ($La^{3+}$). The cations used as the promoters may include inorganic cations complexed with inorganic or organic ligands, e.g. $Pt(NH_3)_6^{4+}$ and $Cr(NH_3)_6^{2+}$.

For nucleic acid denaturation such a promoter may be any inorganic or organic molecule which increases the rate or extent of denaturation of the double helix. It should be soluble in the chosen reaction medium. It preferably does not affect or interfere with DNA or other materials such as enzymes or oligonucleotide probes which may be present in the solution. Alternatively, the promoter may be immobilised to or included in material from which the electrode is constructed.

The additional promoter may be a water-soluble compound of the bipyridyl series, especially a viologen such as methyl-viologen or a salt thereof. Whilst the mechanism of operation of such promoters is presently not known with certainty, it is believed that the positively charged viologen molecules interact between the negatively charged nucleic acid such as DNA and the negatively charged cathode to reduce electrostatic repulsion therebetween and hence to promote the approach of the DNA to the electrode surface where the electrical field is at its strongest. Accordingly, one preferred option is to employ as promoters compounds having spaced positively charged centres, e.g. bipolar positively charged compounds. Preferably the spacing between the positively charged centres is similar to that in viologens. Other suitable viologens include ethyl-viologen, isopropyl-viologen and benzyl-viologen.

The ionic strength of said solution is preferably no more than 250 mM, more preferably no more than 100 mM. As it has been found that the rate of denaturation increases as the ionic strength is decreased, the said ionic strength is still more preferably no more than 50 mM, e.g. no more than 25 mM or even no more than 5 mM. Generally, the lower the ionic strength, the more rapid is the denaturation. However, in calculating ionic strength for these purposes it may be appropriate to ignore the contribution to ionic strength of any component which acts as a promoter as described above.

The electrode may be a so called "modified electrode" in which the denaturing is promoted by a compound coated on to, or adsorbed on to, or incorporated into the structure of the electrode which is otherwise of an inert but conducting material.

A first preferred form of electrochemical cell for use in this invention is described below which uses a carbon rod electrode dipping into a carbon block containing a well. In an alternative electrochemical cell configuration, working, counter and optionally reference electrodes may be formed on a single surface, e.g. a flat surface by any printing method such as thick film screen printing, ink jet printing, or by using a photo-resist followed by etching. It is also possible that the counter and reference electrodes can be combined on the flat surface leading to a two electrode configuration. Alternatively the electrodes may be formed on the inside surface of a well which is adapted to hold liquid, such a well could be the well known 96 well or Microtitre plate, it may also be a test tube or other vessel. Electrode arrays in Microtitre plates or other moulded or thermoformed plastic materials may be provided for multiple nucleic acid denaturation experiments or other disassociation reactions. The reactin may be carried out on a damp porous member, e.g. filter paper.

Nucleic acid strand separation may be carried out in an aqueous medium or in a mixture of water with an organic solvent such as dimethylformamide. The use of polar solvents other than water or non-polar solvents is also accepted but is not preferred. The process may be carried out at ambient temperatures or if desired temperatures up to adjacent the pre-melting temperature of the nucleic acid.

The denaturing process carried out on nucleic acids according to the invention may be incorporated as a step in a number of more complex processes, e.g. procedures involving the analysis and/or the amplification of nucleic acid. Some examples of such applications are described below.

The invention includes a process for detecting the presence or absence of a predetermined nucleic acid sequence in a sample which comprises: denaturing a sample of double-stranded nucleic acid by means of an electrode; hybridising the denatured nucleic acid with an oligonucleotide probe for the sequence; and determining whether the said hybridisation has occurred, wherein during denaturation the solution contains a said buffer.

Thus, the invented process has application in DNA and RNA hybridisation where a specific gene sequence is to be indentified e.g. specific to a particular organism or specific to a particular hereditary disease of which sickle cell anaemia is an example. To detect a specific sequence it is first necessary to prepare a sample of DNA, preferably of purified DNA, means for which are known, which is in native double-stranded form. It is then necessary to convert the double-stranded DNA to single-stranded form before a hybridisation step with a labelled nucleotide probe which has a complementary sequence to the DNA sample can take place. The denaturation process of the invention can be used for this purpose in a preferred manner by carrying out the following steps:

denaturing a sample of DNA by applying a voltage by means of an electrode to the sample DNA in contact with a said buffer in solution;

hybridising the denatured DNA with a directly labelled or indirectly labelled nucleotide probe complementary to the sequence of interest; and determining whether the hybridisation has occurred, which determination may be by detecting the presence of the probe, the probe being directly radio-labelled, fluorescent labelled, chemiluminescent labelled or enzyme-labelled or being an indirectly labelled probe which carries biotin for example to which a labelled avidin or avidin type molecule can be bound later.

In a typical DNA probe assay it is customary to immobilise the sample DNA to a membrane surface which may be composed of neutral or charged nylon or nitrocellulose. The immobilisation is achieved by charge interactions or by baking the membrane containing DNA in an oven. The sample DNA can be heated to high temperature to ensure conversion to single-stranded form before binding to the membrane or it can be treated with alkali once on the membrane to ensure conversion to the single-stranded form. The disadvantages of the present methods are:

heating to high temperatures to create single-stranded DNA can cause damage to the sample DNA itself;

the use of alkali requires an additional step of neutralisation before hybridisation with the labelled probe can take place.

One improved method for carrying out DNA probe hybridisation assays is the so called "sandwich" technique where a specific oligonucleotide is immobilised on a surface. The surface having the specific oligonucleotide thereon is then hybridised with a solution containing the target DNA in a single-stranded form, after which a second labelled oligonucleotide is then added which also hybridises to the target DNA. The surface is then washed to remove unbound labelled oligonucleotide, after which any label which has become bound to target DNA on the surface can be detected later.

This procedure can be simplified by using the disassociation process of the invention to denature the double-stranded DNA into the required single-stranded DNA. The working electrode, counter electrode and optionally a reference electrode and/or the promoter can be incorporated into a test tube or a well in which the DNA probe assay is to be carried out. The DNA sample, promoter if not already present and oligonucleotide probes can then be added and the voltage applied to denature the DNA. The resulting single-stranded DNA is hybridised with the specific oligonucleotide immobilised on the surface after which the remaining stages of a sandwich assay are carried out. All the above steps can take place without a need for high temperatures or addition of alkali reagents as in the conventional process.

The electrochemical denaturation of DNA can be used in the amplification of nucleic acids, e.g. in a polymerase chain reaction, ligase chain reaction amplification procedure or a strand displacement amplification technique. Thus the present invention provides a process for replicating a nucleic acid which comprises: separating the strands of a sample double-stranded nucleic acid in contact with or dissolved in a solution containing a said buffer under the influence of an electrical voltage applied to the solution from an electrode; hybridising the separated strands of the nucleic acid with at least one oligonucleotide primer that hybridises with at least one of the strands of the denatured nucleic acid; synthesising an extension product of an or each primer which is sufficiently complementary to the respective strand of the nucleic acid to hybridise therewith; and separating the or each extension product from the nucleic acid strand with which it is hybridised to obtain the extension product.

In such a replication procedure mediated by polymerase, e.g. a polymerase chain reaction procedure, it may not be necessary in all cases to carry out denaturation to the point of producing wholly single-stranded molecules of nucleic acid. It may be sufficient to produce a sufficient local and/or temporary weakening or separation of the double helix in the primer hybridisation site to allow the primer to bind to its target. Once the primer is in position on a first of the target strands, rehybridisation of the target strands in the primer region will be prevented and the other target strands may be progressively displaced by extension of the primer or by further temporary weakening or separation processes.

Preferably, the said amplification process further comprises repeating the procedure defined above cyclicly, e.g. for more than 10 cycles, e.g. up to 20 or 30 cycles. In the amplification process the hybridisation step is preferably carried out using two primers which are complementary to different strands of the nucleic acid.

The denaturation to obtain the extension products as well as the original denaturing of the target nucleic acid is preferably carried out by applying to the solution of the nucleic acid a voltage between electrodes, the solution containing a buffer as described herein.

The process may be a standard or classical PCR process for amplifying at least one specific nucleic acid sequence contained in a nucleic acid or a mixture of nucleic acids wherein each nucleic acid consists of two separate complementary strands, of equal or unequal length, which process comprises:

(a) treating the strands with two oligonucleotide primers, for each different specific sequence being applied, under conditions such that for each different sequence being amplified an extension product of each primer is synthesised which is complementary to each nucleic acid strand, wherein said primers are selected so as to be substantially complementary to different strands of each specific sequence such that the extension product synthesised from one primer, when it is separated from its complement, can serve as a template for synthesis of the extension produce of the other primer;

(b) separating the primer extension products from the templates on which they were synthesised to produce single-stranded molecules in the presence of a said promoter by applying a voltage from an electrode to the reaction mixture;

(c) treating the single-stranded molecules generated from step (b) with the primers of step (a) under conditions such that a primer extension product is synthesised using each of the single strands produced in step (b) as a template.

Alternatively, the process may be any variant of the classical or standard PCR process, e.g. the so-called "inverted" or "inverse" PCR process or the "anchored" PCR process.

The invention therefore includes an amplification process as described above in which a primer is hybridised to a circular nucleic acid and is extended to form a duplex which is denatured by the denaturing process of the invention, the amplification process optionally being repeated through one or more additional cycles.

More generally, the invention includes a process for replicating a target sequence of nucleic acid comprising hybridisation, extension and denaturation of nucleic acid (e.g. cycles of hybridising and denaturing) wherein said denaturation is produced by operating on a solution containing said nucleic acid with an electrode in the presence of a said buffer.

The process of the invention is applicable to the ligase chain reaction. Accordingly, the invention includes a process for amplifying a target nucleic acid comprising the steps of:

(a) providing nucleic acid of a sample as single-stranded nucleic acid;

(b) providing in the sample at least four nucleic acid probes, wherein:

i) the first and second of said probes are primary probes, and the third and fourth of said probes are secondary nucleic acid probes;

ii) the first probe is a single strand capable of hybridising to a first segment of a primary strand of the target nucleic acid;

iii) the second probe is a single strand capable of hybridising to a second segment of said primary strand of the target nucleic acid;

iv) the 5' end of the first segment of said primary strand of the target is positioned relative to the 3' end of the second segment of said primary strand of the target to enable joining of the 3' end of the first probe to the 5' end of the second probe, when said probes are hybridised to said primary strand of said target nucleic acid;

v) the third probe is capable of hybridising to the first probe; and vi) the fourth probe is capable of hybridising to the second probe; and (c) repeatedly or continuously:

i) hybridising said probes with nucleic acid in said sample;

ii) ligating hybridised probes to form reorganised fused probe sequences; and iii) denaturing DNA in said sample by applying a voltage from an electrode to the reaction mixture in the presence of a said buffer.

In all of the amplification procedures described above the denaturation of the DNA to allow subsequent hybridisation with the primers can be carried out by the application of an appropriate potential to the electrode. The process may be carried out stepwise involving successive cycles of denaturation or renaturation as in the existing thermal methods of PCR and LCR, but it is also possible for it to be carried out continuously since the process of chain extension or ligation by the enzyme and subsequent strand separation by the electrochemical process can continue in the same reaction as nucleic acid molecules in single-stranded form will be free to hybridise with primers once they leave the denaturing influence of the electrode. Thus, provided that the primer will hybridise with the DNA an extension or ligation product will be synthesised. The electrochemical DNA amplification technique can be used analytically to detect and analyse a very small sample of DNA e.g. a single copy gene in an animal cell or a single cell of a bacterium.

The time required for denaturation to occur may be extremely short, e.g. less than 0.5 second up to 1.0 second. A process of repeated denaturation of double-stranded nucleic acid may be performed, in which said voltage is applied as a repeating pulse having a duration of up to 2 minutes, e.g. up to one minute or much less.

Between said pulses the voltages may be turned off and/or reversed for a period similar to or equal to the period for which the voltage is applied, e.g. the voltage may be applied as pulses at a frequency of from 0.01 to 10 Hz. A single denaturation may be performed using a single pulse cycle.

The voltage may be applied such that there are, in other any order, periods of application of voltage with a first polarity, periods of application of voltage with the opposite polarity to said first polarity and periods of substantially reduced applied voltage. The cycles may be from 0.01 seconds to 5 minutes or more in length, e.g. from 1 second to 5 minutes in length.

Preferably, the periods during which said voltage is applied with a first polarity and said periods during which said voltage is applied with a second polarity are each independently from 0.5 seconds to 1 minute.

Preferably, the periods during which said voltage is substantially reduced are each independently from 0.5 seconds to 3 minutes.

The invention includes a kit for use in a process of disassociating interacting molecules which kit comprises, an electrode, a counter electrode and optionally a reference electrode, and a said buffer.

The kit may further include any or all of one or more oligonucleotide probes, an enzyme such as polymerase, one or more primers, or a disassociation promoter, e.g. a source of lithium ions. The probe, if present, may be labelled in any of the ways discussed above.

The reassociation of molecules, particularly the rehybridisation of nucleic acid strands may be produced or promoted by the application of a reverse voltage using a similar buffer and other conditions as described herein in relation to disassociation.

The invention will now be described with reference to the following drawings and examples.

Figure 3:
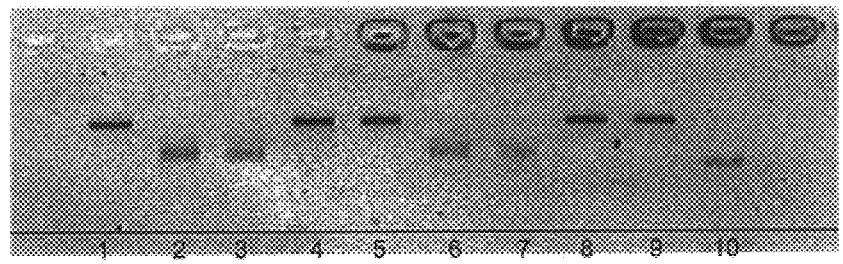
Figure 3:
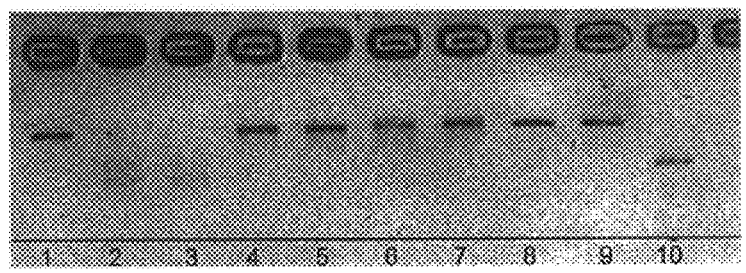
Figure 3C:
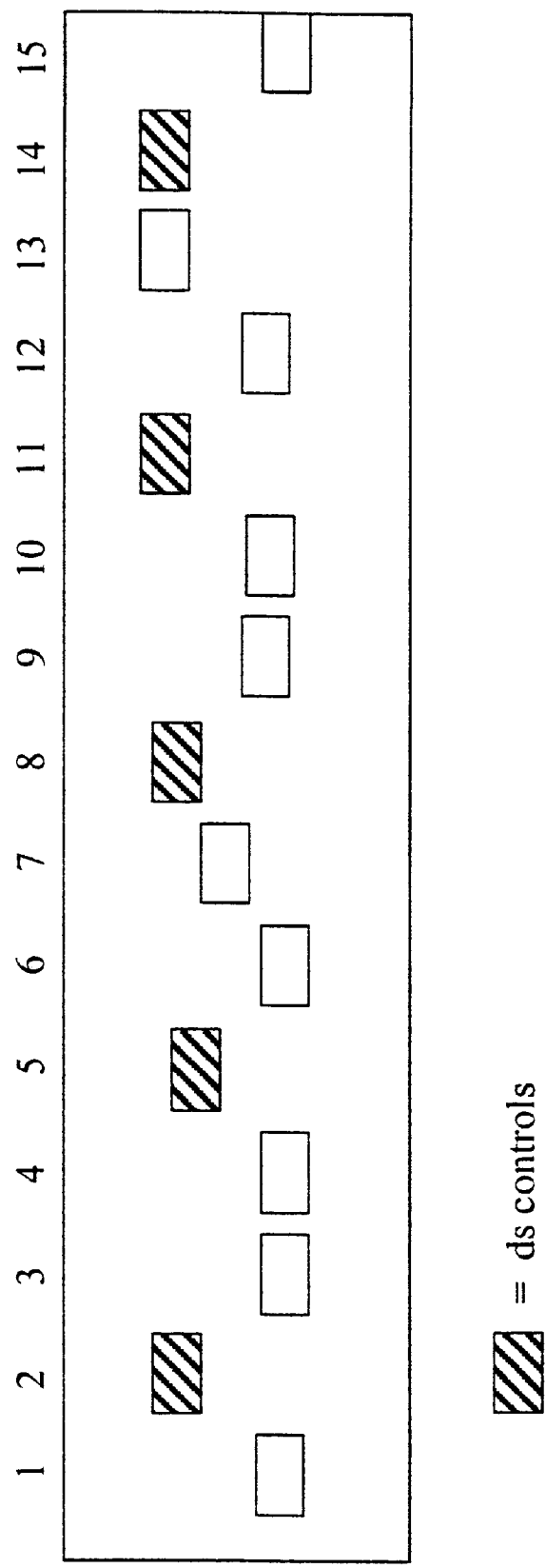

FIGS. 3A–C show three gels obtained in Example 1. Double-stranded control in lane 1, CHES in lanes 2 & 3, MOPS in lanes 4 & 5, CAPS in lanes 6 & 7, HEPES in lanes 8 & 9, and heat-denatured control in lane 10 for FIG. 3A. Double-stranded control in lane 1, Tris-HCl in lanes 2 & 3, PIPES in lanes 4 & 5, TES in lanes 6 & 7, carbonate in lanes 8 & 9, and heat-denatured control in lane 10 for FIG. 3B. Double-stranded control in lane 1, Tris-HCl in lanes 2 & 3, PIPES in lanes 4 & 5, TES in lanes 6 & 7, carbonate in lanes 8 & 9, and heat-denatured control in lane 10 for FIG. 3B. Water in lane 1; double-stranded controls in lanes 2, 5, 8, 11 & 14 (striped band); single-stranded controls in lanes 3, 6, 9, 12 & 15; CAPSO (pH 8) in lane 4; CAPS (pH 8) in lane 7; CHES (pH 7.5) in lane 10; and Tris-HCl (pH 7.5) in lane 13 for FIG. 3C (all at 5 mm).

Figure 4:
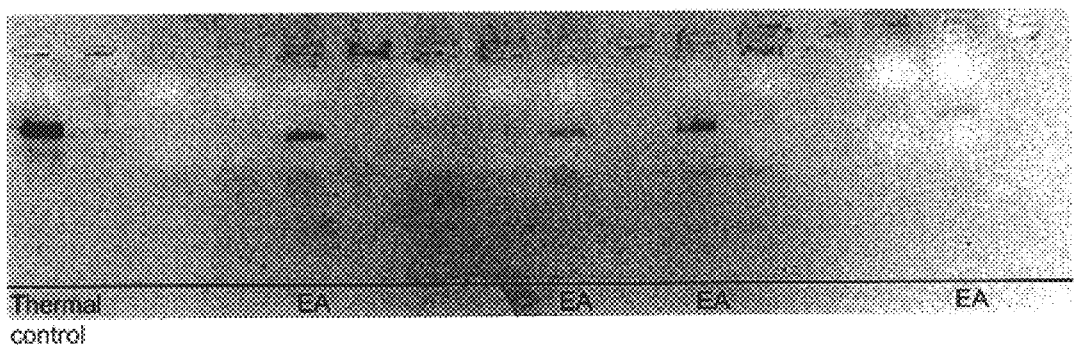

FIG. 4 shows a gel obtained in Example 2 (EA=Electrical Amplification).

Figure 1:
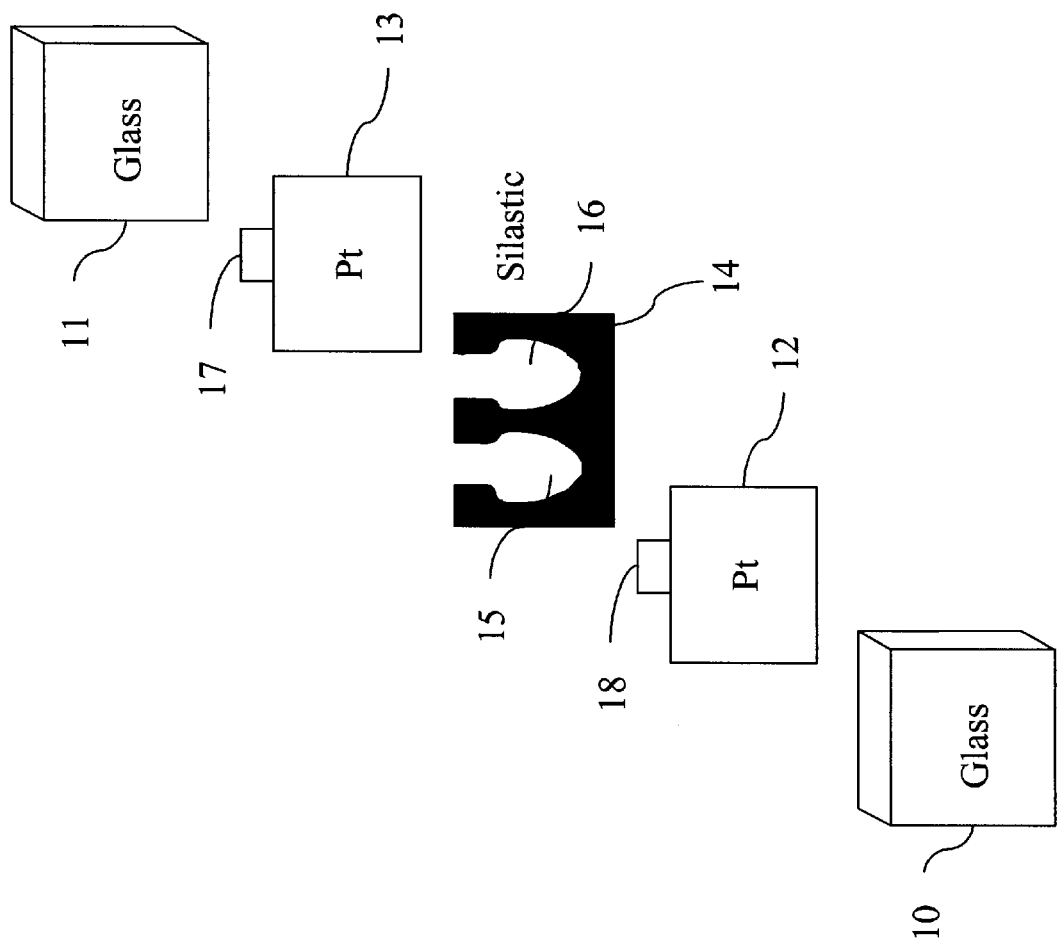
FIG. 1 is an exploded view diagram of an electrochemical cell used for denaturation of DNA.

The cell shown in FIG. 1 comprises a sandwich formed between a pair of opposed glass plates 10, 11 outside a pair of opposed platinum foil electrodes 12, 13 which lie either side of a spacer sheet of a silicone elastomer (silastic™). A pair of chambers 15, 16 are formed in the silastic™ sheet. Each chamber consists of a circular cut-out of diameter approximately 10 mm and a lead-in channel extending to the edge of the sheet. The silastic™ sheet is approximately 400 μm in thickness. Each electrode is provided with a connecting tag 17, 18 by which electrical connection is made to it.

The provision of two cavities in the silastic™ sheet enables the conduct of two reactions according to the invention, or one such reaction with a control, simultaneously.

Thus, it can be seen that illustrated electrochemical cell comprises two opposing planar platinum electrodes. The electrodes are separated by a sheet of deformable insulating material (in this instance a silicone elastomer) which forms a seal against liquid loss, and which is cut to form the electrode chamber. The electrodes are backed by flat plates, and the whole is clamped together between aluminium blocks (not shown) comprising the elastomer sheet from a free state thickness of about 500 μm. The potential difference between the electrodes and the polarity reversal pattern over time are set on a PC, which controls a power supply. The electrode assemblies are maintained at the operating temperature (suitably 55° C.) by standing them on a heating block of appropriate temperature.

The cell shown in FIG. 1 is used in the following examples.

EXAMPLE 1

Figure 2:
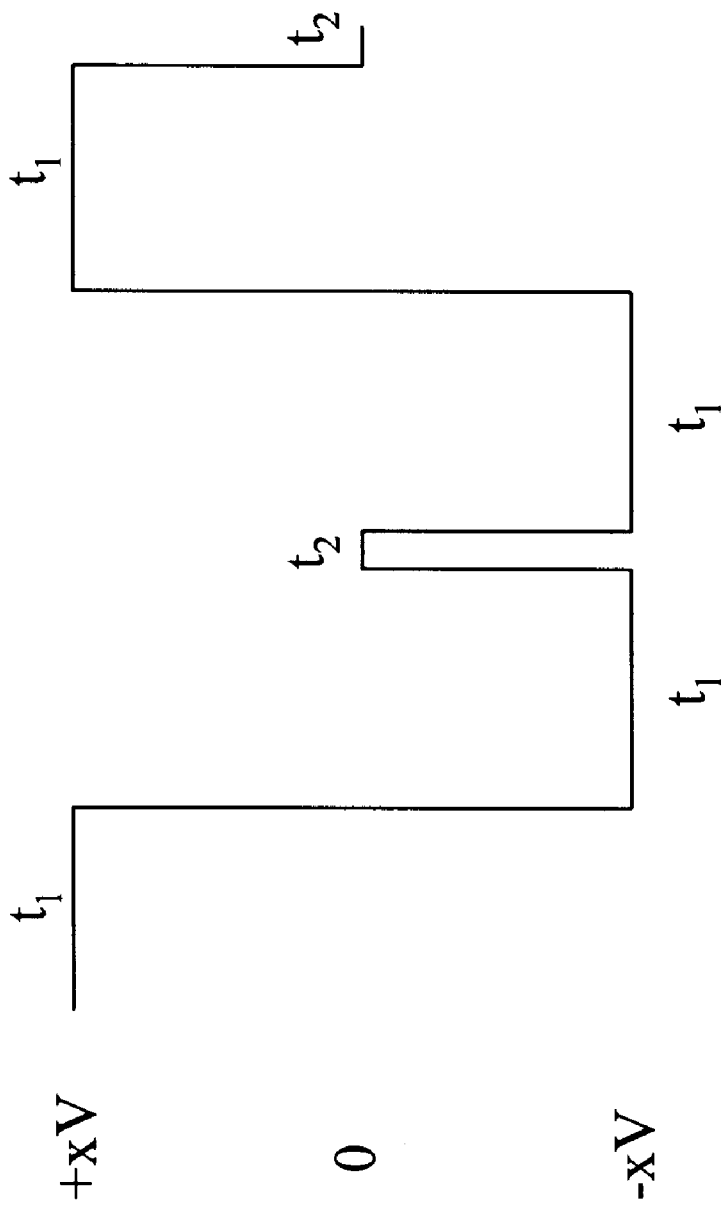
FIG. 2 shows a time/voltage profile suitable for use in operation of the cell of FIG. 1.

In this example electrical denaturation is performed in the electrochemical cell by applying a potential between the electrodes. 45 μl of linearised pUC 18 plasmid (2868 base pairs) a 0.5 μg/ml in water or buffer is placed in the cell. A potential difference is applied across the electrodes for a fixed time period, with or without a number of polarity changes. A typical "profile" is illustrated in FIG. 2 where x=1.2 V $t_1$=3 sec and $t_2$=1 sec. The sample is then removed from the cell and subjected to agarose gel electrophoresis. Denaturation is judged to have occurred when a downward shift in the position of the band is observed.

FIGS. 3A–C show three gels containing pUC DNA in some of the buffers tested, after exposure to the electrical profile in FIG. 2. Successful denaturation occurred in CHES, CAPS, CAPSO and in the control samples denatured by heat. Tris-HCl resulted in diffuse bands, and the other buffers were ineffective. All buffers were used at 5 mM and pH 7.5 except for CAPS at pH 8.0.

EXAMPLE 2

This is a PCR method performed in an electrochemical cell in which an applied potential replaces heat as the denaturing agent. Forty-five μl of reaction mix contained template DNA (0.5 ng linearised pUC), 200 μM each dNTP, 0.2 μM each primer (to give an amplicon of 375 base pairs), 0.5 U VENT DNA polymerase (New England Biolabs Inc.), 0.1% TRITON X-100 octylphenol ethylene oxide condensate, 3 mM $MgSO_4$, in 10 mM CHES buffer, pH 7.5. Twenty cycles were used with the electrical profile shown in FIG. 2, where x=0.5 V, but with a 60 s period of 0 V after each cycle to allow annealing of the primers and extension of the strands.

Amplification was achieved, and is illustrated in FIG. 4, showing four repeats and a control. The identity of the bands produced in electrical amplification was confirmed by:

- visual evaluation on ethidium bromide-stained gels;
- extraction of the sample with phenol-chloroform-ISA and precipitation from the aqueous phase with ethanol, and reappearance of the band when run on a gel;
- detection of the biotinylated amplicon in an assay in which the amplicon is captured on a streptavidin plate, melted to single-strandedness, hybridised to specific DIG-labelled probes which are visualised by the addition of an anti-DIG antibodies conjugated to a colourigenic enzyme;
- the non-appearance of the band (in agarose gels) following treatment of the electrically generated amplicon with DNAse.

What is claimed is:

1. A process for denaturing nucleic acid molecules, comprising subjecting a liquid containing said nucleic acid molecules to an electrical voltage applied between electrodes under conditions such as to wholly or partially denature at least a proportion of said nucleic acid molecules in the presence of a buffer selected from the group consisting of N-cyclohexyl-2-aminoethane sulphonic acid (CHES), N-cyclohexyl-3-aminoethane sulphonic acid (CAPS), and N-cyclohexyl-3-amino-2-hydroxypropane sulphonic acid (CAPSO).

2. The process of claim 1, wherein said buffer has a $pK_a$ of not less than 8.5.

3. The process of claim 1, wherein said buffer has a $pK_a$ of not less than 9.0.

4. The process of claim 1, wherein said buffer has a $pK_a$ of not less than 9.4.

5. The process of claim 1, conducted at a pH of from 7 to 9.

6. The process of claim 1, conducted in from a 5 to 10 mM concentration of said buffer.

7. The process of claim 6, wherein the electrodes approach to within 0.5 mm to one another.

8. The process of claim 1, wherein a voltage of from 0.5 to 3 volts is applied between said electrodes.

9. The process of claim 8, wherein a voltage of from 1.5 to 2.5 volts is applied between said electrodes.

10. A process of repeated denaturation of nucleic acid molecules, wherein said nucleic acid molecules are denatured by a process comprising subjecting a liquid containing said nucleic acid molecules to an electrical voltage applied between electrodes under conditions such as to wholly or partially denature at least a proportion of said nucleic acid molecules in the presence of a buffer selected from the group consisting of N-cyclohexyl-2-aminoethane sulphonic acid (CHES), N-cyclohexyl-3-aminoethane sulphonic acid (CAPS), and N-cyclohexyl-3-amino-2-hydroxypropane sulphonic acid (CAPSO), in which said voltage is applied as a repeating pulse having a duration of up to 2 minutes.

11. The process of claim 10, wherein said voltage is applied as repeating pulse having a duration of up to 1 minute.

12. The process of claim 10, wherein between said pulses the voltage is turned off and/or reversed for a period equal to the period for which the voltage is applied.

13. The process of claim 12, wherein said voltage is applied as pulses at a frequency of from 0.01 to 10 Hz.

14. The process of claim 10, wherein said voltage is applied such that there are, in any order, periods of application of voltage with a first polarity, periods of application of voltage with the opposite polarity to said first polarity and periods of reduced applied voltage.

15. The process of claim 14, wherein said cycles are from 1 second to 5 minutes in length.

16. The process of claim 15, wherein the periods during which said voltage is applied with a first polarity and said periods during which said voltage is applied with a second polarity are each independently of from 0.5 seconds to 1 minute.

17. The process of claim 15, wherein the periods during which said voltage is reduced are each individually from 0.5 seconds to 3 minutes.

18. A process of amplifying a target sequence of nucleic acid comprising hybridisation, extension and denaturation of nucleic acid wherein said denaturation is conducted by subjecting said nucleic acid to a voltage applied between electrodes in the presence of a buffer selected from the group consisting of N-cyclohexyl-2-aminoethane sulphonic acid (CHES), N-cyclohexyl-3-aminoethane sulphonic acid (CAPS), and N-cyclohexyl-3-amino-2-hydroxypropane sulphonic acid (CAPSO).

19. The process of claim 18, which is a PCR or LCR amplification.

20. The process of claim 18, wherein said buffer has a $pK_a$ of not less than 8.5.

21. The process of claim 18, wherein said buffer has a $pK_a$ of not less than 9.0.

22. The process of claim 18, wherein said buffer has a $pK_a$ of not less than 9.4.

23. The process of claim 18, conducted at a pH of from 7 to 9.

24. The process of claim 18, conducted in from a 5 to 10 mM concentration of said buffer.

25. The process of claim 24, wherein the electrodes approach to within 0.5 mm to one another.

26. The process of claim 18, wherein a voltage of from 0.5 to 3 volts is applied between said electrodes.

27. The process of claim 26, wherein a voltage of from 1.5 to 2.5 volts is applied between said electrodes.

28. A kit for use in a process of denaturing nucleic acid molecules which comprises an electrode, a counter electrode, optionally a reference electrode, and a buffer selected from the group consisting of N-cyclohexyl-2-aminoethane sulphonic acid (CHES), N-cyclohexyl-3-aminoethane sulphonic acid (CAPS), and N-cyclohexyl-3-amino-2-hydroxypropane sulphonic acid (CAPSO).

* * * * *